(12) United States Patent
Perez et al.

(10) Patent No.: US 8,257,276 B2
(45) Date of Patent: Sep. 4, 2012

(54) LANCET DEVICE HAVING CAPILLARY ACTION

(75) Inventors: Edward P. Perez, Redwood City, CA (US); Steven N. Roe, San Mateo, CA (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 17 days.

(21) Appl. No.: 12/708,105

(22) Filed: Feb. 18, 2010

(65) Prior Publication Data
US 2010/0145229 A1    Jun. 10, 2010

Related U.S. Application Data

(63) Continuation of application No. 10/838,156, filed on Apr. 30, 2004, now Pat. No. 7,803,123, which is a continuation of application No. 10/054,270, filed on Jan. 22, 2002, now Pat. No. 6,866,675.

(60) Provisional application No. 60/263,533, filed on Jan. 22, 2001.

(51) Int. Cl.
*A61B 5/00*        (2006.01)
*A61B 17/14*       (2006.01)
*A61B 17/32*       (2006.01)
*B65D 81/00*       (2006.01)

(52) U.S. Cl. ......... 600/583; 600/584; 606/181; 606/182

(58) Field of Classification Search .......... 600/573–583; 606/181–182
See application file for complete search history.

(56) References Cited

U.S. PATENT DOCUMENTS

| | | | |
|---|---|---|---|
| 2,646,799 | A | 7/1953 | Jacoby |
| 2,714,890 | A | 8/1955 | Vang |
| 3,086,288 | A | 4/1963 | Balamuth et al. |
| 3,208,452 | A | 9/1965 | Stern |
| 3,673,475 | A | 6/1972 | Britton, Jr. |
| 3,832,776 | A | 9/1974 | Sawyer |
| 4,077,406 | A | 3/1978 | Sandhage et al. |
| 4,154,228 | A | 5/1979 | Feldstein et al. |
| D254,444 | S | 3/1980 | Levine |
| 4,203,446 | A | 5/1980 | Hofert et al. |
| 4,223,674 | A | 9/1980 | Fluent et al. |

(Continued)

FOREIGN PATENT DOCUMENTS

DE    2 131 297    1/1973
(Continued)

OTHER PUBLICATIONS

U.S. Appl. No. 10/607,347 Office Action mailed Apr. 29, 2009.

*Primary Examiner* — Max Hindenburg
*Assistant Examiner* — Adam Eiseman
(74) *Attorney, Agent, or Firm* — Woodard, Emhardt, Moriarty, McNett & Henry LLP

(57) ABSTRACT

A device for sampling body fluid, the device comprising, a main body, a lancet disposed within the main body, a carrier disposed within the main body fixedly attached to the lancet, a biasing means in communication with the lancet and the carrier, an annular space disposed within the main body adjacent the lancet, and a means for measuring a body fluid. Wherein the means for measuring the body fluid may include micro-porous test strips, an electronic testing device, an optical/reflectance testing measuring device, or a visual inspection.

20 Claims, 10 Drawing Sheets

U.S. PATENT DOCUMENTS

| | | |
|---|---|---|
| 4,230,118 A | 10/1980 | Holman et al. |
| 4,356,826 A | 11/1982 | Kubota |
| 4,360,016 A | 11/1982 | Sarrine |
| 4,375,815 A | 3/1983 | Burns |
| 4,392,933 A | 7/1983 | Nakamura et al. |
| 4,449,529 A | 5/1984 | Burns et al. |
| 4,462,405 A | 7/1984 | Ehrlich |
| 4,469,110 A | 9/1984 | Slama |
| 4,503,856 A | 3/1985 | Cornell et al. |
| 4,517,978 A | 5/1985 | Levin et al. |
| 4,518,384 A | 5/1985 | Tarello et al. |
| 4,535,773 A | 8/1985 | Yoon |
| 4,553,541 A | 11/1985 | Burns |
| 4,577,630 A | 3/1986 | Nitzsche et al. |
| 4,627,445 A | 12/1986 | Garcia et al. |
| 4,637,403 A | 1/1987 | Garcia et al. |
| 4,653,513 A | 3/1987 | Dombrowski |
| 4,677,979 A | 7/1987 | Burns |
| 4,750,489 A | 6/1988 | Berkman et al. |
| 4,787,398 A * | 11/1988 | Garcia et al. .................. 600/583 |
| 4,794,926 A | 1/1989 | Munsch et al. |
| 4,823,806 A | 4/1989 | Bajada |
| 4,850,973 A | 7/1989 | Jordan et al. |
| 4,858,607 A | 8/1989 | Jordan et al. |
| 4,869,249 A | 9/1989 | Crossman et al. |
| 4,883,068 A | 11/1989 | Dechow |
| 4,920,977 A | 5/1990 | Haynes |
| 4,924,879 A | 5/1990 | O'Brien |
| 4,983,178 A | 1/1991 | Schnell |
| 4,990,154 A | 2/1991 | Brown et al. |
| 4,994,079 A | 2/1991 | Genese et al. |
| 4,995,402 A | 2/1991 | Smith et al. |
| 5,001,054 A | 3/1991 | Wagner |
| 5,014,718 A | 5/1991 | Mitchen |
| 5,029,583 A | 7/1991 | Meserol et al. |
| 5,035,704 A | 7/1991 | Lambert et al. |
| 5,047,044 A | 9/1991 | Smith et al. |
| 5,059,394 A | 10/1991 | Phillips et al. |
| 5,070,886 A | 12/1991 | Mitchen et al. |
| 5,097,810 A | 3/1992 | Fishman et al. |
| 5,100,620 A | 3/1992 | Brenneman |
| 5,145,565 A | 9/1992 | Kater et al. |
| 5,152,775 A | 10/1992 | Ruppert |
| 5,163,442 A | 11/1992 | Ono |
| 5,188,118 A | 2/1993 | Terwilliger |
| 5,189,751 A | 3/1993 | Giuliani et al. |
| 5,217,480 A | 6/1993 | Haber et al. |
| 5,222,504 A | 6/1993 | Solomon |
| 5,231,993 A | 8/1993 | Haber et al. |
| 5,279,294 A | 1/1994 | Anderson et al. |
| 5,298,224 A | 3/1994 | Plum |
| 5,318,583 A | 6/1994 | Rabenau et al. |
| 5,318,584 A | 6/1994 | Lange et al. |
| 5,320,607 A | 6/1994 | Ishibashi |
| 5,320,808 A | 6/1994 | Holen et al. |
| 5,322,609 A | 6/1994 | Graham |
| 5,368,047 A | 11/1994 | Suzuki et al. |
| 5,395,387 A | 3/1995 | Burns |
| 5,402,798 A | 4/1995 | Swierczek et al. |
| 5,415,169 A | 5/1995 | Siczek et al. |
| 5,423,847 A | 6/1995 | Strong et al. |
| 5,472,427 A | 12/1995 | Rammler |
| 5,474,084 A | 12/1995 | Cunniff |
| 5,510,266 A | 4/1996 | Bonner et al. |
| 5,514,152 A | 5/1996 | Smith |
| 5,518,006 A | 5/1996 | Mawhirt et al. |
| 5,529,074 A | 6/1996 | Greenfield |
| 5,531,757 A | 7/1996 | Kensey et al. |
| 5,540,709 A | 7/1996 | Ramel |
| 5,554,166 A | 9/1996 | Lange et al. |
| 5,569,287 A | 10/1996 | Tezuka et al. |
| 5,575,403 A | 11/1996 | Charlton et al. |
| 5,582,184 A | 12/1996 | Erickson et al. |
| 5,607,401 A | 3/1997 | Humphrey |
| 5,628,765 A | 5/1997 | Morita |
| 5,630,986 A | 5/1997 | Charlton et al. |
| 5,632,410 A | 5/1997 | Moulton et al. |
| 5,636,640 A | 6/1997 | Staehlin |
| 5,657,760 A | 8/1997 | Ying et al. |
| 5,662,127 A | 9/1997 | De Vaughn |
| 5,682,233 A | 10/1997 | Brinda |
| 5,700,695 A | 12/1997 | Yassinzadeh et al. |
| 5,714,390 A | 2/1998 | Hallowitz et al. |
| 5,720,924 A | 2/1998 | Eikmeier et al. |
| 5,738,244 A | 4/1998 | Charlton et al. |
| 5,741,288 A * | 4/1998 | Rife .............................. 606/181 |
| RE35,803 E | 5/1998 | Lange et al. |
| 5,755,733 A | 5/1998 | Morita |
| 5,758,643 A | 6/1998 | Wong et al. |
| 5,776,157 A | 7/1998 | Thorne et al. |
| 5,788,651 A | 8/1998 | Weilandt |
| 5,798,031 A | 8/1998 | Charlton et al. |
| 5,800,781 A | 9/1998 | Gavin et al. |
| 5,801,057 A | 9/1998 | Smart et al. |
| 5,810,199 A | 9/1998 | Charlton et al. |
| 5,823,973 A | 10/1998 | Racchini et al. |
| 5,829,589 A | 11/1998 | Nguyen et al. |
| 5,830,219 A | 11/1998 | Bird et al. |
| 5,846,490 A | 12/1998 | Yokota et al. |
| 5,854,074 A | 12/1998 | Charlton et al. |
| 5,855,801 A | 1/1999 | Lin et al. |
| 5,857,983 A | 1/1999 | Douglas et al. |
| 5,860,922 A | 1/1999 | Gordon et al. |
| 5,863,800 A | 1/1999 | Eikmeier et al. |
| 5,871,494 A | 2/1999 | Simons et al. |
| 5,873,887 A | 2/1999 | King et al. |
| 5,879,311 A | 3/1999 | Duchon et al. |
| 5,880,829 A | 3/1999 | Kauhaniemi et al. |
| 5,885,211 A | 3/1999 | Eppstein et al. |
| 5,891,053 A | 4/1999 | Sesekura |
| 5,902,279 A | 5/1999 | Powles et al. |
| 5,916,229 A | 6/1999 | Evans |
| 5,935,075 A | 8/1999 | Casscells et al. |
| 5,938,679 A | 8/1999 | Freeman et al. |
| 5,947,957 A | 9/1999 | Morris |
| 5,951,492 A | 9/1999 | Douglas et al. |
| 5,951,493 A | 9/1999 | Douglas et al. |
| 5,951,582 A | 9/1999 | Thorne et al. |
| 5,968,063 A | 10/1999 | Chu et al. |
| 5,971,941 A | 10/1999 | Simons et al. |
| 5,997,561 A | 12/1999 | Bocker et al. |
| 5,997,817 A | 12/1999 | Crismore et al. |
| 6,022,324 A | 2/2000 | Skinner |
| 6,027,459 A | 2/2000 | Shain et al. |
| 6,036,924 A | 3/2000 | Simons et al. |
| 6,048,352 A | 4/2000 | Douglas et al. |
| 6,051,392 A | 4/2000 | Ikeda et al. |
| 6,056,701 A | 5/2000 | Duchon et al. |
| 6,063,039 A | 5/2000 | Cunningham et al. |
| 6,071,249 A | 6/2000 | Cunningham et al. |
| 6,071,251 A | 6/2000 | Cunningham et al. |
| 6,071,294 A | 6/2000 | Simons et al. |
| 6,090,078 A | 7/2000 | Erskine |
| 6,093,156 A | 7/2000 | Cunningham et al. |
| 6,099,484 A | 8/2000 | Douglas et al. |
| 6,117,630 A | 9/2000 | Reber et al. |
| 6,120,462 A | 9/2000 | Hibner et al. |
| 6,120,676 A | 9/2000 | Heller et al. |
| 6,132,449 A | 10/2000 | Lum et al. |
| 6,136,013 A | 10/2000 | Marshall et al. |
| 6,139,562 A | 10/2000 | Mauze et al. |
| 6,143,164 A | 11/2000 | Heller et al. |
| 6,146,361 A | 11/2000 | DiBiasi et al. |
| 6,152,889 A | 11/2000 | Sopp et al. |
| 6,152,942 A | 11/2000 | Brenneman et al. |
| 6,155,992 A | 12/2000 | Henning et al. |
| 6,156,051 A | 12/2000 | Schraga |
| 6,159,424 A | 12/2000 | Kauhaniemi et al. |
| 6,171,325 B1 | 1/2001 | Mauze et al. |
| 6,176,865 B1 | 1/2001 | Mauze et al. |
| 6,183,489 B1 | 2/2001 | Douglas et al. |
| 6,193,673 B1 | 2/2001 | Viola et al. |
| 6,203,504 B1 | 3/2001 | Latterell et al. |
| 6,206,841 B1 | 3/2001 | Cunningham et al. |
| 6,210,420 B1 | 4/2001 | Mauze et al. |
| 6,210,421 B1 | 4/2001 | Bocker et al. |
| 6,228,100 B1 | 5/2001 | Schraga |

| | | |
|---|---|---|
| 6,231,531 B1 | 5/2001 | Lum et al. |
| 6,258,229 B1 | 7/2001 | Winarta et al. |
| 6,261,241 B1 | 7/2001 | Burbank et al. |
| 6,261,245 B1 | 7/2001 | Kawai et al. |
| 6,270,637 B1 | 8/2001 | Crismore et al. |
| 6,283,926 B1 | 9/2001 | Cunningham et al. |
| 6,285,454 B1 | 9/2001 | Douglas et al. |
| 6,306,104 B1 | 10/2001 | Cunningham et al. |
| 6,306,152 B1 | 10/2001 | Verdonk et al. |
| 6,315,738 B1 | 11/2001 | Nishikawa et al. |
| 6,319,210 B1 | 11/2001 | Douglas et al. |
| 6,332,871 B1 | 12/2001 | Douglas et al. |
| 6,352,514 B1 | 3/2002 | Douglas et al. |
| 6,358,265 B1 | 3/2002 | Thorne, Jr. et al. |
| 6,364,889 B1 | 4/2002 | Kheiri et al. |
| 6,364,890 B1 | 4/2002 | Lum et al. |
| 6,375,627 B1 | 4/2002 | Mauze et al. |
| 6,379,317 B1 | 4/2002 | Kintzig et al. |
| 6,379,969 B1 | 4/2002 | Mauze et al. |
| 6,391,005 B1 | 5/2002 | Lum et al. |
| 6,402,701 B1 | 6/2002 | Kaplan et al. |
| 6,402,704 B1 | 6/2002 | McMorrow |
| 6,409,740 B1 | 6/2002 | Kuhr et al. |
| 6,461,496 B1 | 10/2002 | Feldman et al. |
| 6,472,220 B1 | 10/2002 | Simons et al. |
| 6,485,439 B1 | 11/2002 | Roe et al. |
| 6,488,891 B2 | 12/2002 | Mason et al. |
| 6,491,709 B2 | 12/2002 | Sharma et al. |
| 6,497,845 B1 | 12/2002 | Sacherer |
| 6,503,210 B1 | 1/2003 | Hirao et al. |
| 6,506,575 B1 | 1/2003 | Knappe et al. |
| 6,530,892 B1 | 3/2003 | Kelly |
| 6,551,494 B1 | 4/2003 | Heller et al. |
| 6,561,989 B2 | 5/2003 | Whitson |
| 6,576,101 B1 | 6/2003 | Heller et al. |
| 6,607,658 B1 | 8/2003 | Heller et al. |
| 6,612,111 B1 | 9/2003 | Hodges et al. |
| 6,783,502 B2 | 8/2004 | Orloff et al. |
| 6,866,675 B2 | 3/2005 | Perez et al. |
| 7,041,068 B2 | 5/2006 | Freeman et al. |
| 2001/0031931 A1 | 10/2001 | Cunningham et al. |
| 2001/0039387 A1 | 11/2001 | Rutynowski et al. |
| 2002/0002344 A1 | 1/2002 | Douglas et al. |
| 2002/0004196 A1 | 1/2002 | Whitson |
| 2002/0040230 A1 | 4/2002 | Kuhr et al. |
| 2002/0052618 A1 | 5/2002 | Haar et al. |
| 2002/0082522 A1 | 6/2002 | Douglas et al. |
| 2002/0082543 A1 | 6/2002 | Park et al. |
| 2002/0103499 A1 | 8/2002 | Perez et al. |
| 2002/0130042 A1 | 9/2002 | Moerman et al. |
| 2002/0137998 A1 | 9/2002 | Smart et al. |
| 2002/0160520 A1 | 10/2002 | Orloff et al. |
| 2002/0168290 A1 | 11/2002 | Yuzhakov et al. |
| 2002/0169393 A1 | 11/2002 | Cunningham et al. |
| 2002/0177761 A1 | 11/2002 | Orloff et al. |
| 2002/0177763 A1 | 11/2002 | Burns et al. |
| 2002/0177788 A1 | 11/2002 | Hodges et al. |
| 2003/0028087 A1 | 2/2003 | Yuzhakov et al. |
| 2003/0028125 A1 | 2/2003 | Yuzhakov et al. |
| 2003/0083685 A1 | 5/2003 | Freeman et al. |
| 2003/0083686 A1 | 5/2003 | Freeman et al. |
| 2003/0088191 A1 | 5/2003 | Freeman et al. |
| 2003/0144608 A1 | 7/2003 | Kojima et al. |
| 2003/0191415 A1 | 10/2003 | Moerman et al. |
| 2003/0196894 A1 | 10/2003 | Cai et al. |
| 2003/0199789 A1 | 10/2003 | Boecker et al. |
| 2003/0199790 A1 | 10/2003 | Boecker et al. |
| 2003/0199791 A1 | 10/2003 | Boecker et al. |
| 2003/0199893 A1 | 10/2003 | Boecker et al. |
| 2003/0199894 A1 | 10/2003 | Boecker et al. |
| 2003/0199896 A1 | 10/2003 | Boecker et al. |
| 2003/0199897 A1 | 10/2003 | Boecker et al. |
| 2003/0199898 A1 | 10/2003 | Boecker et al. |
| 2003/0199899 A1 | 10/2003 | Boecker et al. |
| 2003/0199900 A1 | 10/2003 | Boecker et al. |
| 2003/0199901 A1 | 10/2003 | Boecker et al. |
| 2003/0199902 A1 | 10/2003 | Boecker et al. |
| 2003/0199903 A1 | 10/2003 | Boecker et al. |
| 2003/0199904 A1 | 10/2003 | Boecker et al. |
| 2003/0199906 A1 | 10/2003 | Boecker et al. |
| 2003/0199907 A1 | 10/2003 | Boecker et al. |
| 2003/0199908 A1 | 10/2003 | Boecker et al. |
| 2003/0199909 A1 | 10/2003 | Boecker et al. |
| 2003/0199910 A1 | 10/2003 | Boecker et al. |
| 2003/0199911 A1 | 10/2003 | Boecker et al. |
| 2003/0201194 A1 | 10/2003 | Heller et al. |
| 2003/0211619 A1 | 11/2003 | Olson et al. |
| 2003/0212344 A1 | 11/2003 | Yuzhakov et al. |
| 2003/0212346 A1 | 11/2003 | Yuzhakov et al. |
| 2003/0233112 A1 | 12/2003 | Alden et al. |
| 2003/0233113 A1 | 12/2003 | Alden et al. |
| 2004/0009100 A1 | 1/2004 | Simons et al. |
| 2004/0055898 A1 | 3/2004 | Heller et al. |
| 2004/0087990 A1 | 5/2004 | Boecker et al. |
| 2004/0120848 A1 | 6/2004 | Teodorczyk |

FOREIGN PATENT DOCUMENTS

| | | |
|---|---|---|
| DE | 24 61 273 | 9/1976 |
| DE | 28 03 345 | 6/1979 |
| EP | 0 988 828 | 3/2000 |
| EP | 1 281 352 | 2/2003 |
| EP | 1 374 770 A1 | 1/2004 |
| FR | 289191 | 11/1953 |
| GB | 1080986 | 8/1967 |
| JP | H02-111275 | 4/1990 |
| JP | H04-194660 | 7/1992 |
| JP | 09-084781 | 3/1997 |
| JP | 09-089885 | 4/1997 |
| JP | 09-168530 | 6/1997 |
| JP | H09-276235 | 10/1997 |
| JP | H09-294737 | 11/1997 |
| JP | 09-313465 | 12/1997 |
| JP | H10-005198 | 1/1998 |
| JP | H10-005199 | 1/1998 |
| JP | H10-005200 | 1/1998 |
| JP | H10-014906 | 1/1998 |
| JP | H10-024028 | 1/1998 |
| JP | H10-033507 | 2/1998 |
| JP | H10-033508 | 2/1998 |
| JP | 2000-116768 | 4/2000 |
| JP | 2000-116768 A2 | 4/2000 |
| JP | 2000-232974 | 8/2000 |
| WO | WO 93/02720 A1 | 2/1993 |
| WO | WO 93/09710 | 5/1993 |
| WO | WO 93/09723 | 5/1993 |
| WO | WO 93/12726 A1 | 7/1993 |
| WO | WO 94/16737 A1 | 8/1994 |
| WO | WO 96/14017 | 5/1996 |
| WO | WO 97/42888 A1 | 11/1997 |
| WO | WO 98/14125 | 4/1998 |
| WO | WO 98/35225 | 8/1998 |
| WO | WO 00/40150 | 7/2000 |
| WO | WO 01/00090 A1 | 1/2001 |
| WO | WO 01/34029 A1 | 5/2001 |
| WO | WO 01/66010 A1 | 9/2001 |
| WO | WO 01/72220 | 10/2001 |
| WO | WO 01/95806 | 12/2001 |
| WO | WO 02/36010 | 5/2002 |
| WO | WO 02/056751 | 7/2002 |
| WO | WO 02/056769 A1 | 7/2002 |
| WO | WO 02/078533 | 10/2002 |
| WO | WO 02/100252 | 12/2002 |
| WO | WO 02/100253 | 12/2002 |
| WO | WO 02/100254 | 12/2002 |
| WO | WO 02/101359 | 12/2002 |
| WO | WO 03/088834 A1 | 10/2003 |
| WO | WO 03/088835 A2 | 10/2003 |
| WO | WO 03/088851 | 10/2003 |
| WO | WO 03/094752 | 11/2003 |
| WO | WO 2004/041082 | 5/2004 |

* cited by examiner

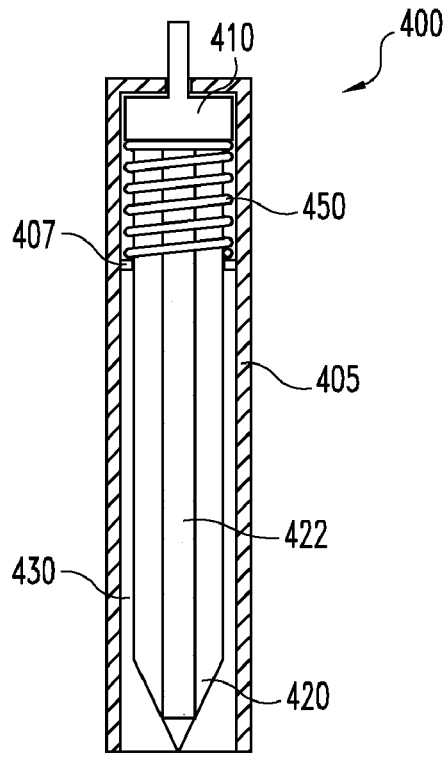
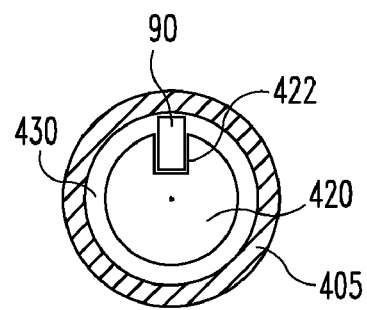
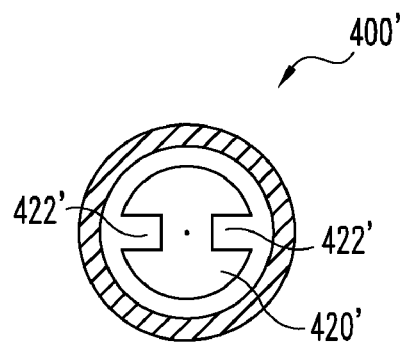
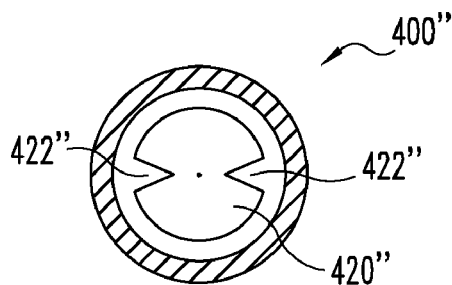
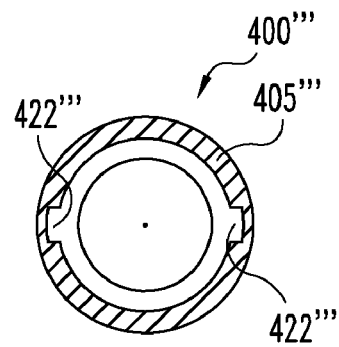
Fig. 4A
Fig. 4B
Fig. 4C
Fig. 4D
Fig. 4E

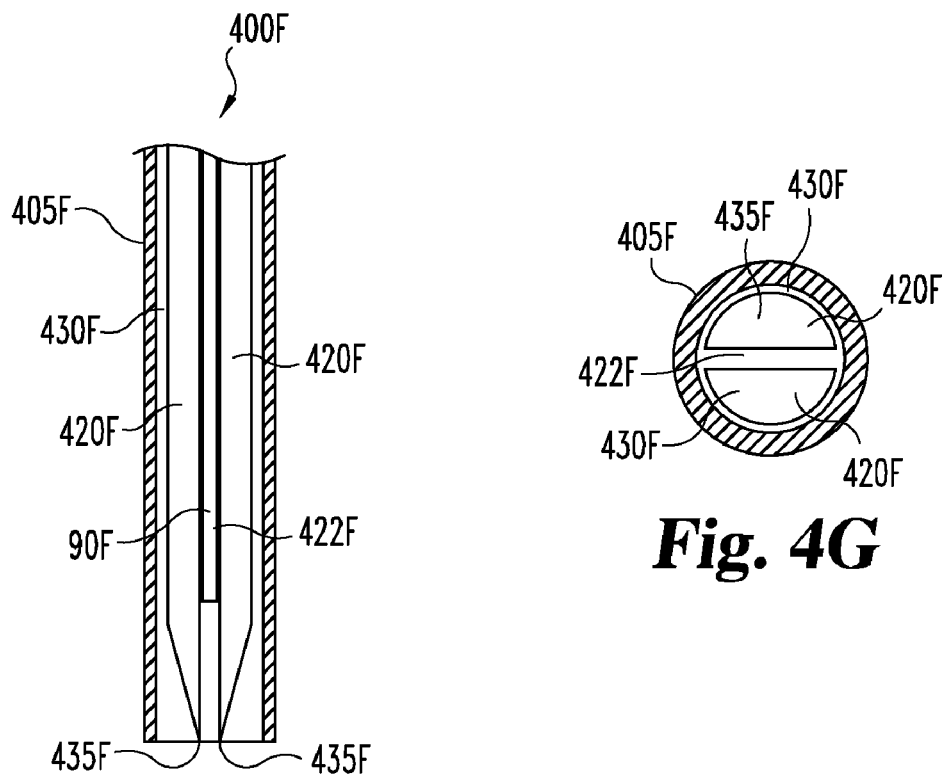
Fig. 4F
Fig. 4G
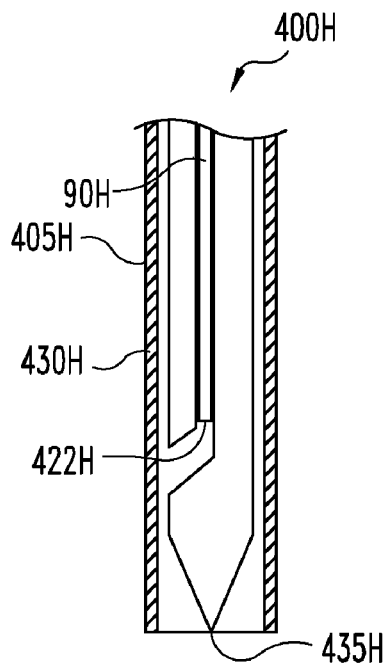
Fig. 4H

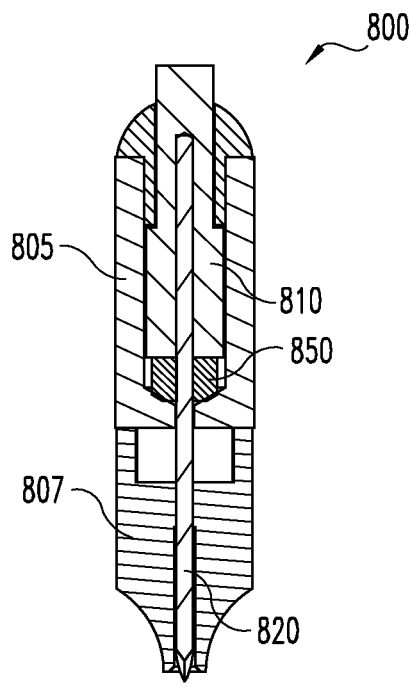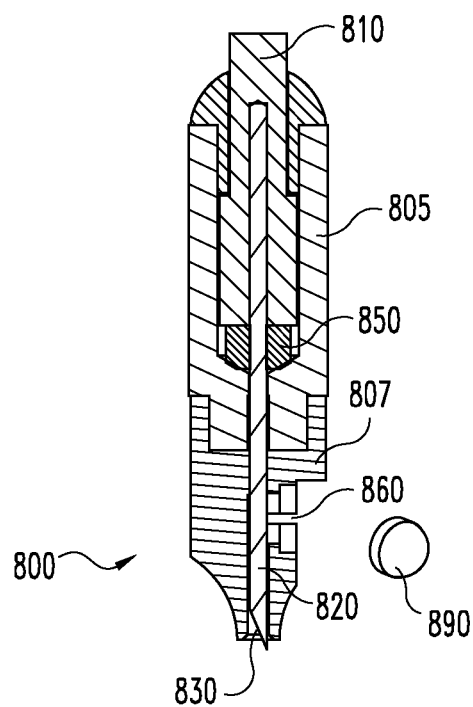
Fig. 8A    Fig. 8B
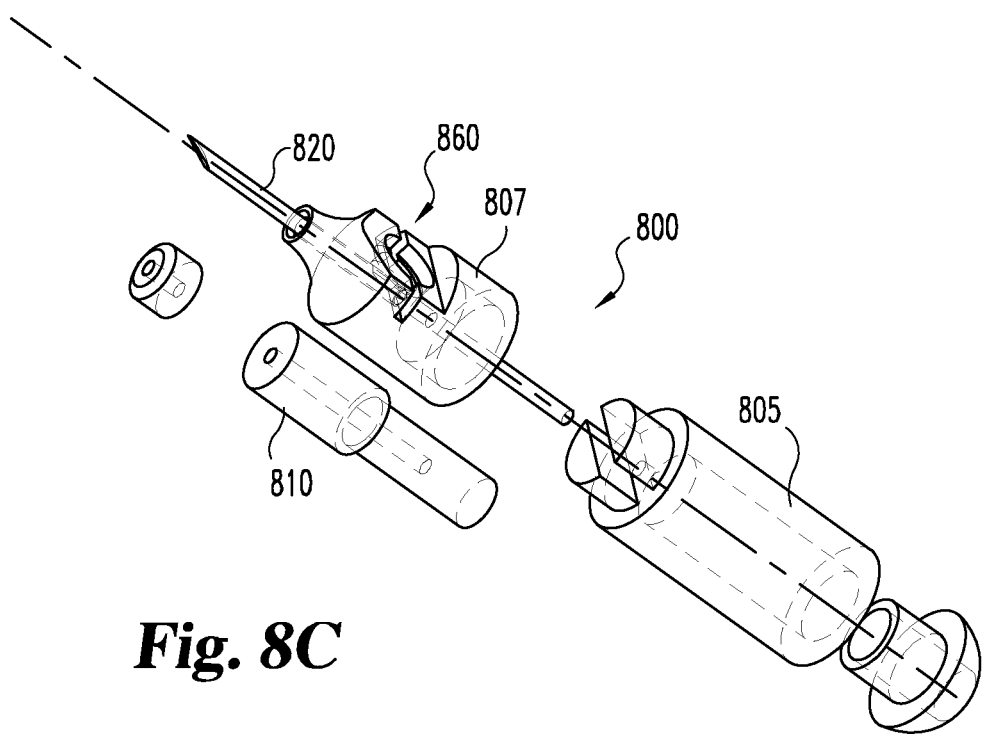
Fig. 8C

LANCET DEVICE HAVING CAPILLARY ACTION

CROSS-REFERENCE TO RELATED APPLICATIONS

The present application is a continuation of U.S. patent application Ser. No. 10/838,156, filed on Apr. 30, 2004, which is a continuation of U.S. patent application Ser. No. 10/054,270, filed on Jan. 22, 2002, now U.S. Pat. No. 6,866,675, which claims the benefit of U.S. Provisional Patent Application No. 60/263,533, filed on Jan. 22, 2001, which are hereby incorporated by reference in their entirety.

FIELD OF THE INVENTION

This invention relates to lancing devices and methods for obtaining samples of blood and body fluids for analysis.

BACKGROUND OF THE INVENTION

Many medical procedures in use today require a relatively small sample of a body fluid, such as blood or interstitial fluid, in the range of less than 50 µL. It is more cost effective and less traumatic to the patient to obtain such a sample by lancing or piercing the skin at a selected location, such as the finger or forearm, to enable the collection of 1 or 2 drops of blood, than by using a phlebotomist to draw a tube of venous blood. With the advent of home use tests for the self monitoring of blood glucose, there is a requirement for a simple procedure which can be performed in any setting without a person needing the assistance of a professional.

Lancets in conventional use generally have a rigid body and a sterile needle which protrudes from one end. The lancet may be used to pierce the skin, thereby enabling the expression of a blood sample. When a capillary tube or test strip is placed adjacent the expressed blood, the fluid can be collected. By a capillary tube fluid is then transferred to a test device, such as a paper testing strip. Blood is most commonly taken from the fingertips, where the supply is generally more accessible. However, the nerve density in this region causes significant pain in many patients. Sampling of alternative sites, such as earlobes and limbs, is sometimes practiced to lessen the pain. However, these sites are also less likely to provide sufficient blood samples and can make blood transfer directly to test devices more difficult. Additionally, it is often difficult for a user to determine whether a sufficiently large drop of body fluid has been expressed at the incision point to provide a sufficient sample.

Prior methods of acquiring a blood sample have suffered from the need to use two components and the resulting time lapse between the lancing action and placement of the capillary tube adjacent the lanced location, potentially allowing contamination or not collecting the fluid expressed from the body. One prior method for addressing this concern was to create a larger opening and/or to force excess fluid from the body. While this assisted in ensuring an adequate fluid supply, it potentially created a large opening to be healed and could cause the patient additional pain. Moreover, use of this method requires precise steps where the lancet is removed and the capillary tube or test strip is then correctly aligned with the lanced location. It is important for correct collection that no gap or movement of the capillary tube relative to the lanced location occur during collection. There is a need for a system to assist in removal of the lancet and placement of the capillary member with a minimum of time and movement. Further, there is a need for a compact, simple system to obtain the desired sample size without the need for excess lancing of tissue, extra pain to the patient or expressing an excess volume of body fluid.

To reduce the anxiety of piercing the skin and the associated pain, many spring loaded devices have been developed. The following two patents are representative of the devices which were developed in the 1980's for use with home diagnostic test products.

U.S. Pat. No. 4,503,856, Cornell et al., describes a spring loaded lancet injector. The reusable device interfaces with a disposable lancet. The lancet holder may be latched in a retracted position. When the user contacts a release, a spring causes the lancet to pierce the skin at high speed and then retract. The speed is important to reduce the pain associated with the puncture.

Levin et al., U.S. Pat. No. 4,517,978 describes a blood sampling instrument. This device, which is also spring loaded, uses a standard disposable lancet. The design enables easy and accurate positioning against a fingertip so the impact site can be readily determined. After the lancet pierces the skin, a bounce back spring retracts the lancet to a safe position within the device.

In home settings it is often desirable to collect a sample in order to enable a user to perform a test at home such as glucose monitoring. Some blood glucose monitoring systems, for example, require that the blood sample be applied to a test device which is in contact with a test instrument. In such situations, bringing the finger to the test device poses some risk of contamination of the sample with a previous sample that may not have been properly cleaned from the device.

Glucose monitoring devices utilize blood samples in many ways, though the two most common methods are a paper strip and a capillary tube. Monitors that utilize a paper strip require the patient to pierce a finger or appropriate location, withdraw a small sample of blood from the piercing, such as by squeezing, and then place the paper strip over the blood sample and wait until the paper strip absorbs the blood. Monitors that utilize a capillary tube require the patient to follow the process described above, except that a paper strip is not utilized to collect the blood from the skin. Instead, a small capillary tube is placed over the sample until a sufficient amount of blood is withdrawn into the capillary tube, which is then tested.

In some instances patients are diabetic, that is they are unable to properly metabolize glucose. In order to regulate insulin levels within their bodies, individuals who are diabetic must inject themselves with an appropriate amount of insulin. To determine the proper amount of insulin, an individual first must test their blood glucose levels. Typically, a patient has to 'prick' a fingertip with a lancet to create an incision through which blood can be withdrawn and placed on a glucose monitoring strip which then reacts and changes colors indicating the glucose level.

Haynes U.S. Pat. No. 4,920,977 describes a blood collection assembly with a lancet and micro-collection tube. This device incorporates a lancet and collection container in a single device. The lancing and collection are two separate activities, but the device is a convenient single disposable unit for situations when sample collection prior to use is desirable. Similar devices are disclosed in Sarrine U.S. Pat. No. 4,360,016 and O'Brian U.S. Pat. No. 4,924,879.

Jordan et al., U.S. Pat. No. 4,850,973 and U.S. Pat. No. 4,858,607 disclose a combination device which may alternatively be used as a syringe-type injection device or a lancing device with disposable solid needle lancet, depending on its configuration.

Lange et al., U.S. Pat. No. 5,318,584 describes a blood lancet device for withdrawing blood for diagnostic purposes. This invention uses a rotary/sliding transmission system to reduce the pain of lancing. The puncture depth is easily and precisely adjustable by the user.

Suzuki et al., U.S. Pat. No. 5,368,047, Dombrowski U.S. Pat. No. 4,654,513 and Ishibashi et al., U.S. Pat. No. 5,320,607 each describe suction-type blood samplers. These devices develop suction between the lancing site and the end of the device with the lancet holding mechanism withdrawing after piercing the skin. A flexible gasket around the end of the device helps seal the device end around the puncture site until an adequate sample is withdrawn from the puncture site or the user pulls the device away.

Garcia et al., U.S. Pat. No. 4,637,403 discloses a combination lancing and blood collection device which uses a capillary action passage to conduct body fluid to a separate test strip in the form of a micro-porous membrane. It is necessary to achieve a precise positioning of the upper end of the capillary passage with respect to the membrane in order to ensure that the body fluid from the passage is transferred to the membrane. If an appreciable gap exists therebetween, no transfer may occur. Also, the diameter of the capillary passage is relatively small, so the width of a sample transferred to the membrane may be too small to be measured by on-site measuring devices such as an optical measuring system or an electrochemical meter.

Single use devices have also been developed for single use tests, i.e. home cholesterol testing, and for institutional use, to eliminate the risk of cross-patient contamination with multi-patient use. Crossman et al., U.S. Pat. No. 4,869,249, and Swierczek U.S. Pat. No. 5,402,798, describe disposable, single use lancing devices.

The disclosures of the above patents are incorporated herein by reference.

An object of the present invention is to provide a disposable lancet unit that may be deployed easily and without causing undue pain.

Another object of the present invention is to provide a one-step system for sampling a body fluid for testing.

Another object of the present invention is to provide an apparatus that withdraws a blood sample and provides an individual with a blood glucose level reading.

A further object of the present invention is to provide an apparatus that does not require the user to perform multiple steps in order to produce a blood glucose level reading.

A further object of the present invention is to provide a lancet unit having capillary functions.

Further objects, features and advantages of the present invention shall become apparent from the detailed drawings and descriptions provided herein.

SUMMARY OF THE INVENTION

The present invention provides a device in the preferred embodiments which combines a lancing element with a capillary member to integrate in a single unit the lancing of a person's skin and the acquisition of the body fluid producing by lancing. The invention employs a lancing element which extends within the capillary member, and the body fluid passes through the capillary member in the space between the lancing element and the interior wall of the capillary.

One aspect of the present invention relates to a sampling device for sampling body fluid. The device includes a lancet, a main body and a carrier device for displacing the lancet. The device defines an annular space disposed about the lancet whereby body fluid is drawn into the annular space through capillary action. In one embodiment, the system further comprises a test strip with a reagent. In one approach, the test strip is in fluid communication with a distal end of the annular space. In another approach, the test strip is disposed within the annular space between the lancet and the main body. In one preferred embodiment, the test strip comprises a micro porous membrane.

In another embodiment the sampling device includes a main body, a lancet, a carrier for the lancet, and at least one channel disposed within the lancet to support a test strip. In this embodiment, the body fluid contacts the test strip as the annular space is filled.

In another embodiment, the sampling system includes a main body, a lancet, a carrier for the lancet and a testing device. The lancet is disposed within the main body, thereby creating an annular space between the lancet and the main body, and is advanced and retracted to allow the main body to fill with fluid. The main body is moved to or connected to a testing device for optical or electro-chemical testing of the fluid.

In a still further embodiment, the sampling system includes a disposable cartridge mounted to a base unit. The base unit includes actuating structure for activating the lancet within the capillary member. Preferably the base unit may be reused and minimizes the materials and structure in the cartridge.

The present invention also relates to a method of sampling body fluid which comprises the steps of positioning the testing device over a testing site, activating the lancet carrying device, whereby the lancet forms a small incision in the testing site through which body fluid flows, drawing the body fluid into the main body of the device to contact a testing strip or sensors, to provide a user with the results.

BRIEF DESCRIPTION OF THE DRAWINGS

FIG. 4A is a cut-away side view of still another preferred alternative embodiment of the present invention.

FIG. 4B is a bottom view of the alternative embodiment of FIG. 4A illustrating a test strip disposed within a groove on the lancet.

FIG. 4C is a bottom view of an alternate embodiment of the lancing and testing apparatus of the present invention.

FIG. 4D is a bottom view of a further alternate embodiment of the apparatus of the present invention.

FIG. 4E is a bottom view of still a further preferred embodiment of the apparatus of the present invention.

FIG. 4F is a cut-away side view of another preferred embodiment of the present invention illustrating a dual lancet apparatus.

FIG. 4G is a cross-sectional end view of the alternate embodiment shown in FIG. 4F.

FIG. 4H is a cut-away side view of another alternate embodiment of the lancet of the present invention.

FIGS. 8A and 8B are cut-away side views of an alternate embodiment of the apparatus of the present invention.

FIG. 8C is a disassembled view of the apparatus of FIGS. 8A and 8B.

DETAILED DESCRIPTION OF PREFERRED EMBODIMENTS

Figure 1A:
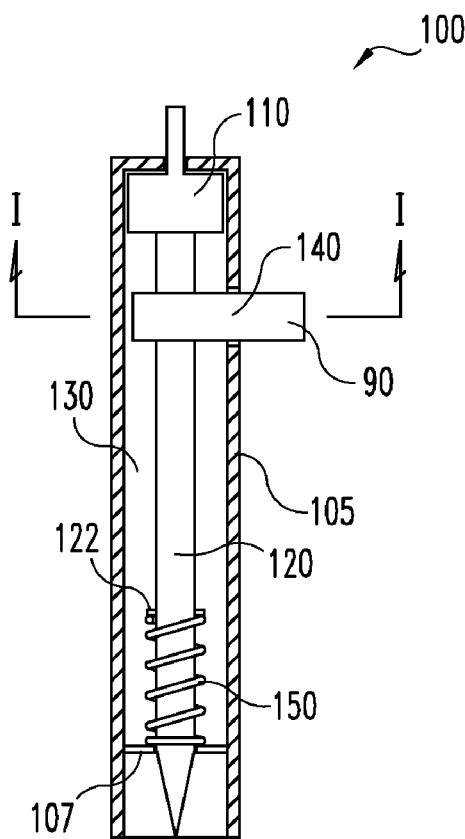
FIG. 1A is a cut-away side view of one apparatus according to a preferred embodiment of the present invention.

For the purposes of promoting an understanding of the principles of the invention, reference will now be made to the embodiments illustrated and specific language will be used to describe the same. It will nevertheless be understood that no limitation of the scope of the invention is thereby intended, such alterations, modifications, and further applications of the principles of the invention being contemplated as would normally occur to one skilled in the art to which the invention relates.

The present invention provides a device and method for obtaining small volume samples of a body fluid. In preferred embodiments the invention combines a lancing element integrated with a capillary member in a single unit for lancing a person's skin and acquiring the body fluid producing by the lancing. The invention employs a lancing element which extends within the capillary member, and the body fluid passes through the capillary member in the space between the lancing element and the interior wall of the capillary member. This integrated unit is useful by itself or in combination with other devices which perform complementary functions such as promoting the expression of the body fluid from the incision, collecting and analyzing or testing the fluid. The device may be a reusable or disposable unit.

In contrast to the prior art, the present invention locates the lancet within the capillary such that the capillary is in position, and centered, over the incision before the lancet is extended to create the incision. This avoids the need for moving the capillary after the incision is made, and consequently reduces the significant difficulties that can be encountered in moving a capillary tube quickly and accurately to the site of an incision. It therefore enhances the ability to acquire the expressed body fluid without loss, delay or contamination.

In view of these purposes and advantages, it will be appreciated by those skilled in the art that the particular mechanisms used to extend and retract the lancet, and to hold the capillary tube, are not critical to the invention, although certain advantages are obtained with given embodiments, as hereafter described. Therefore, the underlying concept forming the basis for the present invention is useful with a wide variety of lancing mechanisms, as are known in the art. For example, the present invention is useful in combination with the mechanisms for extending and retracting lancets relative to a housing described, for example in application PCT/EP01/12527 and U.S. application Ser. No. 09/963,967, incorporated herein by reference. The foregoing disclosures constitute a part of the description of the present invention and its available design alternatives.

The present invention is useful with various body fluids. For example, the unit is suitable for accessing either blood or interstitial body fluid. The device may be readily configured for either fluid by controlling the distance by which the lancing member extends into the user's skin when in the extended position. For example, a depth of 0.5 to 2.5 mm will typically produce blood.

Figure 1B:
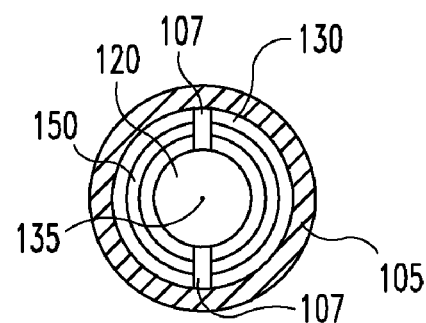
FIG. 1B is a bottom view of the apparatus of FIG. 1A.
Figure 1C:
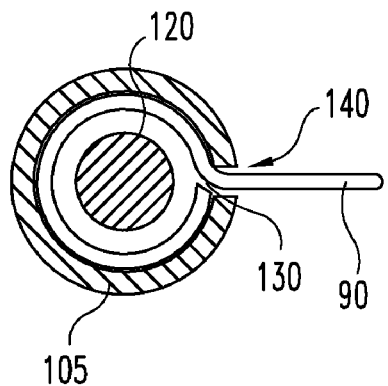
FIG. 1C is a cross-sectional view taken along line A-A of FIG. 1A illustrating a test strip disposed within the testing device.

In one preferred embodiment, illustrated in FIGS. 1A, 1B and 1C, unit 100 comprises a body 105 having associated features to facilitate the use of the unit. Body 105 is a capillary member having an internal diameter sized to draw and retain fluid from a contacted source using capillary action. Body 105 includes internal structure for supporting the lancet 120 and for moving the lancet longitudinally between a first, retracted position and a second, extended position. The unit 100 may also include means relating to the testing of the body fluid as described hereafter.

Referring to FIG. 1A in detail, there is shown a basic, integrated unit 100 for testing body fluids. Apparatus 100 comprises a main body 105, lancet 120 with distal point 135, biasing device 150, and lancet carrier or hub 110. Annular space or void 130 is defined within body 105 and disposed between the lancet 120 and the internal wall of main body 105. This space is generally referred to herein as an "annular" space, although it will be appreciated that the shape of the space will vary depending on the shapes of the lancet and capillary member and the position of the lancet within the capillary member.

For purposes herein, the term annular space is to be understood as encompassing generally the space between the capillary member and the contained lancet, including the variety of physical shapes that the space between the lancet and the capillary member may assume, depending at least in part on the noted possible variations. In certain preferred embodiments, the annular space 130 between lancet 120 and main body 105 is between 10 and 500 μm, and is preferably between 20 and 200 μm to obtain optimal capillary fill time with blood.

Referring now to FIG. 1B there is shown a bottom view of apparatus 100. FIG. 1B illustrates annular space 130 disposed between lancet 120 and main body 105. In use, the annular space 130 performs a capillary function in that body fluid is drawn up through apparatus 100 within annular space 130, with displaced air escaping from the unit through the opposing end of body 105. The body 105 and lancet or lancing element 120 are sized and arranged to provide the desired flow of body fluid through capillary action. This will depend to some extent on the subject body fluid, as well as on other parameters.

In addition, the flow of fluid may be enhanced by forming the lancing member and/or the interior surface of the capillary member from a material which is hydrophilic, which has been treated to be hydrophilic, or which has been coated with a hydrophilic material such as a surfactant or hydrophilic polymers. The surfaces can also be treated using polyamides, oxidation (e.g. corona/plasma treatment); plasma chemical vapor deposition; vacuum vapor deposition of metals, metaloxides or non-metaloxides; or deposition of an element which oxidizes with water. The annular space is therefore sized to provide the desired flow by capillary action with the various influences being taken into account.

Optionally an absorbent pad may be placed between the test strip and the distal end of the capillary passage for wicking body fluid from the annular space to the test strip. In the embodiment where the test strip is disposed within the annular space, no absorbent pad may be needed because the test strip will be in direct contact with the body fluid.

The lancing element or lancet 120 is received and longitudinally movable within the capillary space 130 of unit 100 between a first, retracted position, and a second, extended position. Means are provided for resiliently extending and retracting the lancet in order to make a desired incision and to then withdraw the lancet back into a shielded position.

Various means for extending a lancet relative to a housing are known in the art, and are useful in combination with the present invention. These devices, for example, typically include lancets held by carriers that are spring loaded for movement relative to the surrounding housing. Alternatively, a spring-loaded hammer may be use to impact the lancet carrier in order to drive it in the direction to lance the skin. Examples of such mechanisms are contained in the following U.S. Pat. Nos. 5,951,492; 5,857,983 and 5,964,718. The foregoing disclosures are incorporated herein by reference, and constitute a part of the description of the present invention and its available design alternatives.

These devices typically extend the lancet to a defined extent, such as by moving the lancet to a stop. Such devices frequently are produced with a predefined limit of travel for the lancet, thereby defining a penetration for the lancet into the skin. Alternatively, devices are well known which permit the user to adjust the penetration depth, such as by turning a wheel or other mechanism, with such adjustable devices frequently including a dial or other display which indicates the selected depth. These types of mechanisms are useful in combination with the present invention.

Various means may similarly be employed for retracting the lancet after it has made the incision, and many such mechanisms are known in the art, including the references previously cited and incorporated herein. One example of a retraction means is spring 150 (FIG. 1) surrounding lancet 120 and disposed between bearing surfaces or retainers 107 associated with body 105 and bearing surfaces or retainers 122 associated with lancet 120. Preferably bearing surfaces 107 and 122 are fingers, tabs, flanges, rings, or similar structures which provide sufficient bearing surfaces to retain spring 150 in place without materially impeding capillary fluid flow.

The resilient means is mounted to provide relative movement to retract the lancet into the main body after making the incision. Preferably the resilient means, such as spring 150, is made from a biocompatible material, such as metal, plastic, elastic or a similar material known in the art, which does not react with the sample or interfere with the testing procedure. The resilient means may allow multiple uses if the unit is to be reused, or may be a disposable or one-use mechanism used with disposable or one-use embodiments of the unit.

Figure 7:
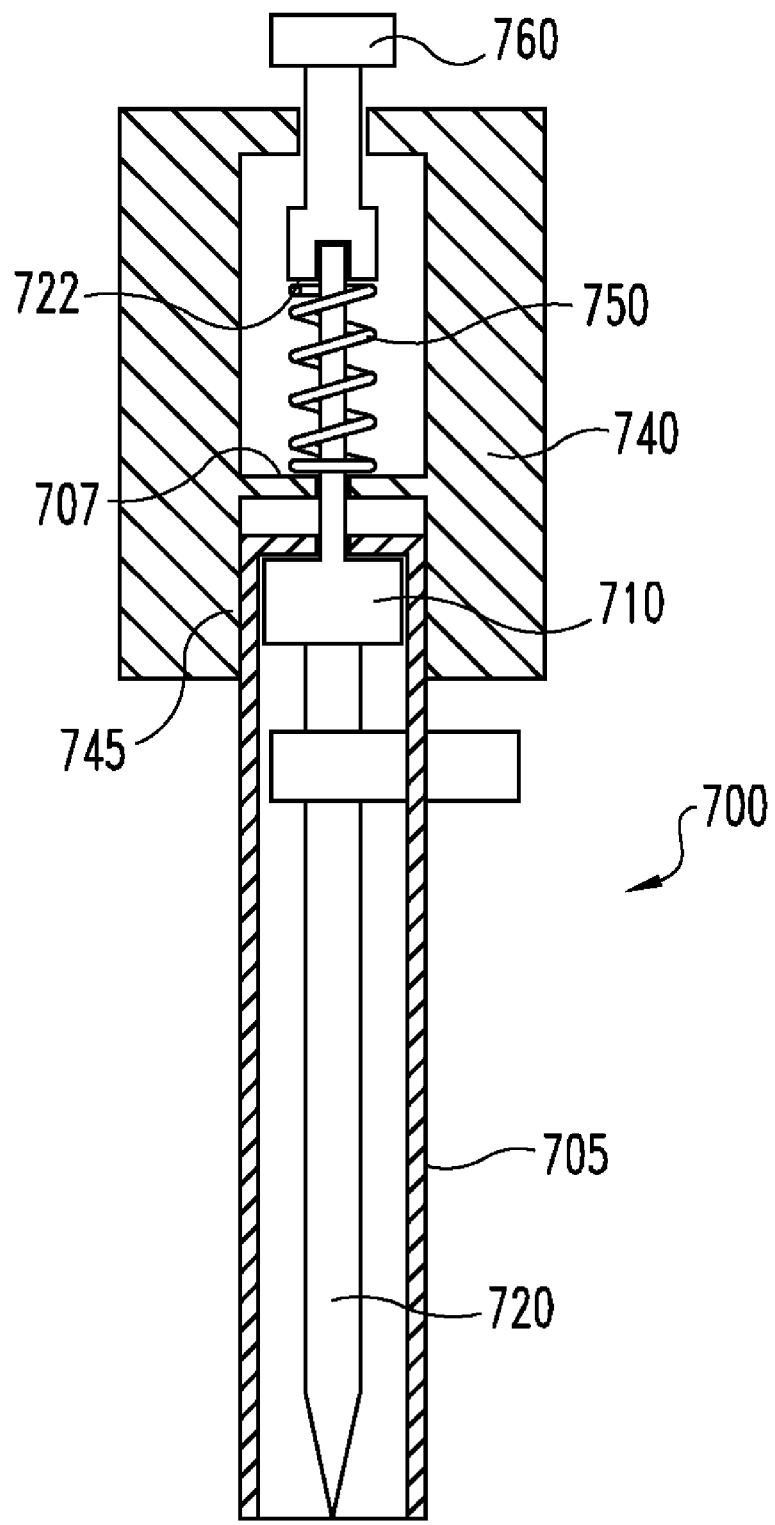
FIG. 7 is a cut-away side view of an alternate preferred embodiment of the apparatus of the present invention.

The resilient means may be placed in various locations without affecting the operation of the unit. For example, the spring may be placed in the lower portion of the main body (FIG. 1A), in the upper portion of the main body (FIG. 4A), externally of the main body between the body and the lancet carrier (not shown) or externally in an external structure holding the unit (FIG. 7). In further alternate embodiments, the resilient means can be arranged to provide expansion or contraction force to move the lancet to its retracted position. Thus, the means for retracting the lancet may, for example, push or pull the lancet to the retracted position.

The withdrawal of the lancet may also be either a full or only a partial withdrawal. When fully withdrawn, the lancet is removed from the incision and returned to the retracted position protected from accidental contact by the user. However, in an alternate approach the lancet could be only partially withdrawn, thereby leaving a portion of the lancet remaining within the incision. When the lancet is only partially withdrawn, the lancet acts as a focal point for locating the blood and transferring it to the capillary. This may be useful to employ the lancet to assure that the incision remains open for the blood or other body fluid to flow out of the incision.

Referring now to FIG. 1C there is shown a cross-sectional view of apparatus 100 taken about line A-A of FIG. 1A. Apparatus 100 further includes a testing element, such as reagent test strip 90 and test strip holder 140. Test strip holder 140 is an opening or slot in the wall of body 105 allowing test strip 90 to be inserted into apparatus 100 and received within annular space 130 such that test strip 90 is disposed radially around lancet 120. Test strip 90 can be held in place during the lancet's movement as shown, or it can move longitudinally with lancet 120 during the lancet's extension and retraction, as shown in later embodiments. Either way, the capillary action of unit 100 draws the body fluid into annular space 130 so that the fluid contacts the test strip.

The body 105 may be made from any suitable material, and typically can be economically produced from plastics, glass, or various other materials, for example by injection molding or extrusion. The main body may be manufactured of a transparent material such as glass, plastic, polyvinyl chloride or any similar bio-compatible plastic. Alternatively, the main body may be manufactured having an opaque or solid appearing surface. In some embodiments it is desirable to have the capillary member transparent, or to include a window portion to allow the user to observe the progress of fluid filling the capillary and/or to facilitate viewing the testing of the body fluid, particularly by optical means.

Lancet 120 and spring 150 may be manufactured of any bio-compatible material such as steel, surgical stainless steel, aluminum, or titanium, as well as many other suitable materials known in the art. Preferably lancet 120 is made in a solid piece which is sufficiently sharpened to create an incision.

Preferably unit 100 is manufactured in a compact size, with annular space 130 sized to hold the desired fluid sample size. While the desired sample size will vary depending on the fluid to be sampled and the specific test desired, in preferred embodiments the volume is relatively small, and may be as small as 3 µL and less, including less than 1 µL. For transport and use, unit 100 may be packaged individually, or may be loaded in a cartridge type of container which may be loaded in an applicator for conducting multiple tests as desired.

Sterility of the unit may be enhanced by the use of a cap (FIG. 5A) or other sealing member placed over the distal end of the capillary member. In one embodiment, a cap is maintained over the capillary member to enclose the lancet prior to use. The cap is simply removed when the unit is to be used. In an alternate embodiment a plastic piece surrounds the tip and a portion of the plastic is twisted, cut or torn off to expose the tip for use.

In a further alternate approach, a membrane is positioned over the distal end of the capillary member to provide a seal for the unit. The membrane is composed of a suitable material through which the lancet may extend during use. Thus, the sealing membrane does not have to be removed for use, but rather is sufficiently thin and penetrable as to remain in place when the lancing member is displaced from the retracted position to the extended position. In the latter embodiment, the sealing membrane is preferably biocompatible as well, and should not interfere with the desired functioning of the lancing member to incise the skin or the resulting capillary fluid flow. One example of such a tip is disclosed in application PCT/EP01/02198.

Figure 2A:
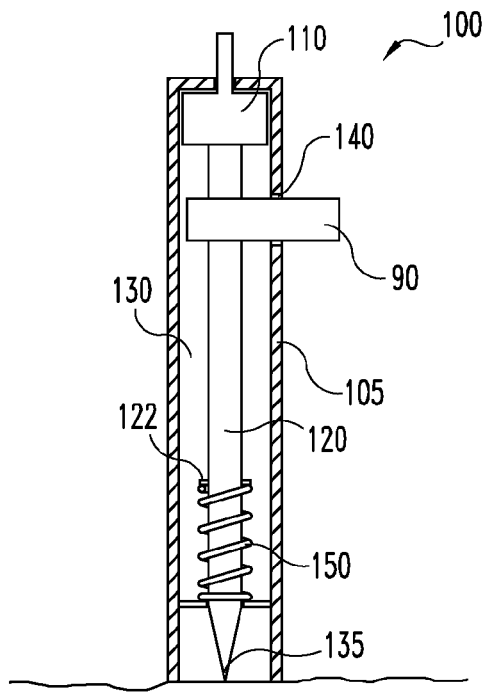
FIGS. 2A, 2B and 2C are cut-away side views of the apparatus of claim 1 in positions during use.
Figure 2B:
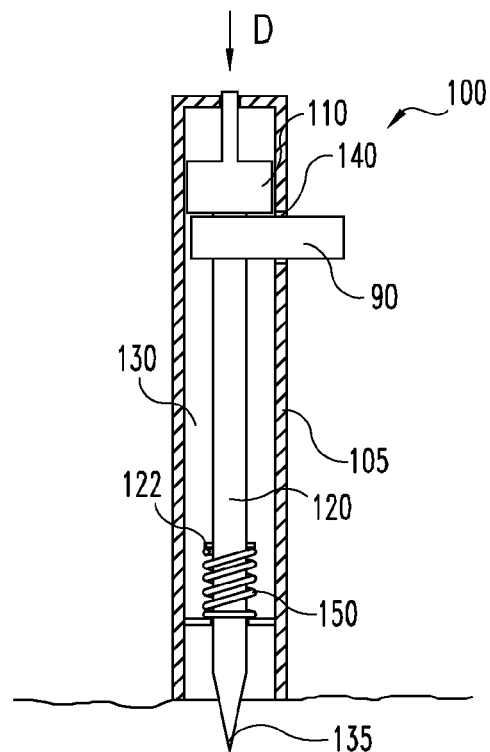
Figure 2C:
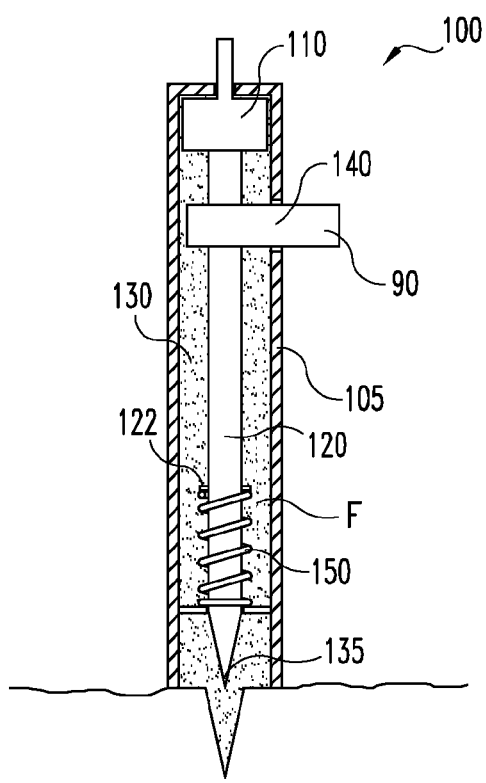

Illustrated in use in FIGS. 2A, 2B and 2C, the distal end of apparatus 100 is placed over an appropriate incision site, such as a forearm or fingertip such that the distal end abuts the skin surface. This provides a position control to enable application of a predetermined (chosen) pricking depth. In the retracted position, the distal tip 135 of the lancing element is fully received within the unit 100, preventing accidental contact with the tip. A downward force D (FIG. 2B) is then applied to lancet carrier 110, displacing lancet 120 from the static, protected position shown in FIG. 2A, to an extended position, shown in FIG. 2B. In the extended position, tip 135 of lancet 120 penetrates the skin tissue thereby creating a small incision, typically 0.5 to 1.2 mm deep. The incision depth will typically be pre-set at a desired level, or may be controlled by a selectable depth adjustment mechanism included on the unit.

The force D is then released from lancet carrier 110, and spring 150 biases lancet 120 into the retracted and protected position as shown in FIG. 2C. After retraction, apparatus 100 remains over the newly formed incision, preferably without movement, as shown in FIG. 2C, and body fluid F is drawn into annular space 130 of device 100 by capillary action. The capillary action is made more efficient since the capillary member is immediately in place and aligned with the incision, minimizing the concerns of movement or a gap between the tissue and the capillary member. A sufficient volume of body fluid F is drawn into annular space 130 so that it may be collected, tested and/or analyzed, for example by contact with test strip 90. In alternate methods of use, additional tools are used to assist in expressing a sufficient volume of fluid from the incision site, as is well known.

Testing of the fluid sample can be accomplished using standard optical or electro-chemical methods. The collected fluid can be analyzed using the full range of available procedures and equipment, including conventional test strip chemistries. For example, in one embodiment, after body fluid F contacts a micro-porous test strip 90, test strip 90 may be optically read in place or after removal to determine, for example, the blood glucose level. An optical reading of the test strip typically compares the color of the reaction of the test strip to a control chart. Alternately, test strip 90 may be removed from apparatus 100 and connected to or placed in a chemical or electronic testing apparatus. In a further alternate embodiment, unit 100 includes an optically-readable, reactive coating placed on the surface of lancet 120 or the interior circumference of body 150. Testing of body fluid F can be accomplished by the optical reading of the result of the reaction of the coating to the body fluid.

Figure 3A:
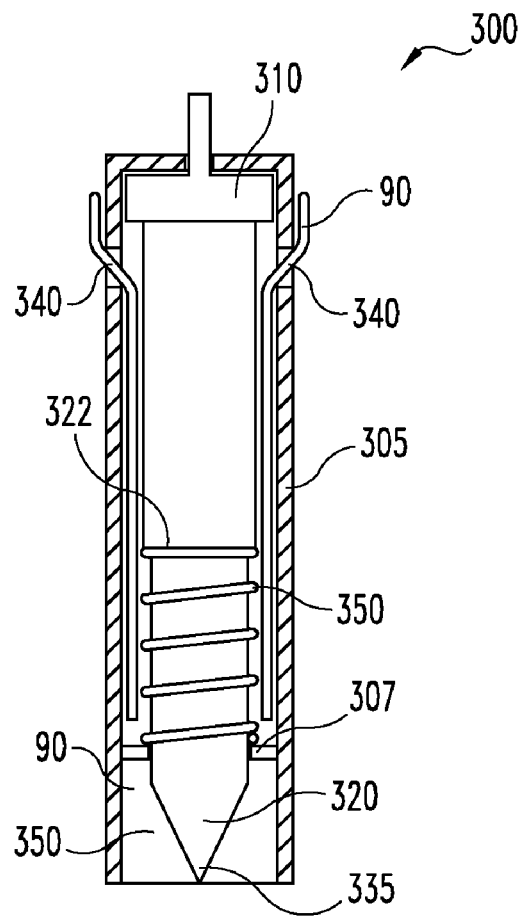
FIG. 3A is a cut-away side view of an alternate preferred embodiment of the present invention.
Figure 3B:
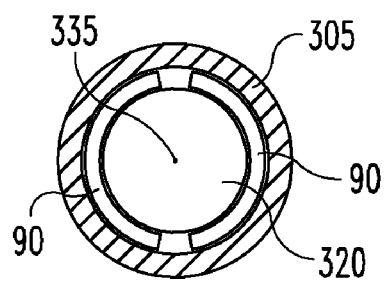
FIG. 3B is a bottom view of the alternate embodiment of FIG. 3A illustrating test strips disposed within the annular space.

The device in alternate embodiments includes multiple testing means, for example two or more test strips 90, and includes alternate structural arrangements. Referring to FIGS. 3A and 3B, an alternative embodiment of apparatus 100 is shown. Apparatus 300 is similar in construction and materials to unit 100 and comprises an outer body 305, lancet 320 having distal tip 335, lancet carrier 310, spring 350, spring bearing surfaces or retainers 307 and 322, and annular space 330. As shown in FIG. 3A and with an upward view in FIG. 3B, apparatus 300 further includes test strip holders 340 and test strips 90 disposed within annular space 330. In use, body fluid that is drawn into annular space 330 by capillary action contacts test strips 90. The multiple test strips 90 can be duplicates to ensure accuracy, or may include different reagents to perform multiple tests simultaneously.

Referring now to FIGS. 4A and 4B there is shown still another embodiment of the apparatus of the present invention. In this embodiment, apparatus 400 comprises main body 405, lancet 420, lancet carrier 410, spring 450, spring retention means 407, groove 422 disposed axially along lancet 420, and annular space 430. As shown in FIG. 4B, test strip 90 is disposed within groove 422 in lancet 420. Although lancet 420 is only shown as having a single groove 422 and a single test strip 90, lancet 420 may include a plurality of grooves and test strips in order to perform the methods of the present invention.

Referring now to FIGS. 4C, 4D and 4E, there are shown alternative embodiments 400', 400" and 400''' of apparatus 400. As shown in FIG. 4C, lancet 420' includes first and second grooves 422', each being adapted to receive a test strip 90 (not shown). Referring to FIG. 4D, lancet 420" includes grooves 422" having a V shaped geometry adapted to receive test strips 90 (not shown). Alternatively, as shown in FIG. 4E, main body 405''' of apparatus 400''' includes grooves 422''' adapted to receive and carry test strips 90 (not shown). Alternately, a reactive coating could be deposited in grooves 422'''. In each of the embodiments illustrated in FIGS. 4C, 4D, and 4E, the apparatus includes each of the man unit elements shown in FIG. 4A.

Referring now to the alternate embodiment in FIGS. 4F and 4G, there is shown apparatus 400F having a main body 405F, first and second lancets 420F, annular space 430F, first and second distal lancet tips 435F and channel 422F formed between first and second lancets 420F. A test strip 90F may be disposed within channel 422F thereby placing the test strip in spatial communication with the body fluid as the fluid moves upwardly into the capillary. Additionally, as lancets 420F are advanced, the test strip 90F will also be advanced.

FIG. 4H shows still another alternative embodiment, unit 400H. Lancet 420H includes channel 422H disposed therein. Channel 422H may be utilized to advance body fluid to a test strip disposed adjacent to the proximal end of the channel. Alternatively, a test strip 90H is disposed within channel 422H.

Figure 5A:
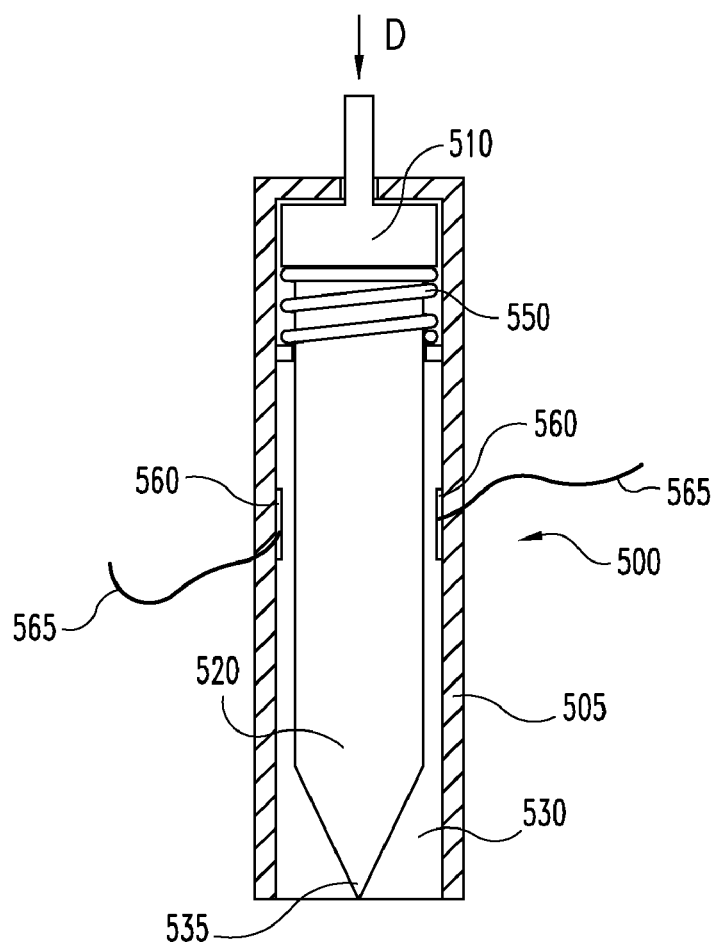
FIG. 5A is a cut-away side view of still another alternate embodiment of the apparatus of the present invention.
Figure 5B:
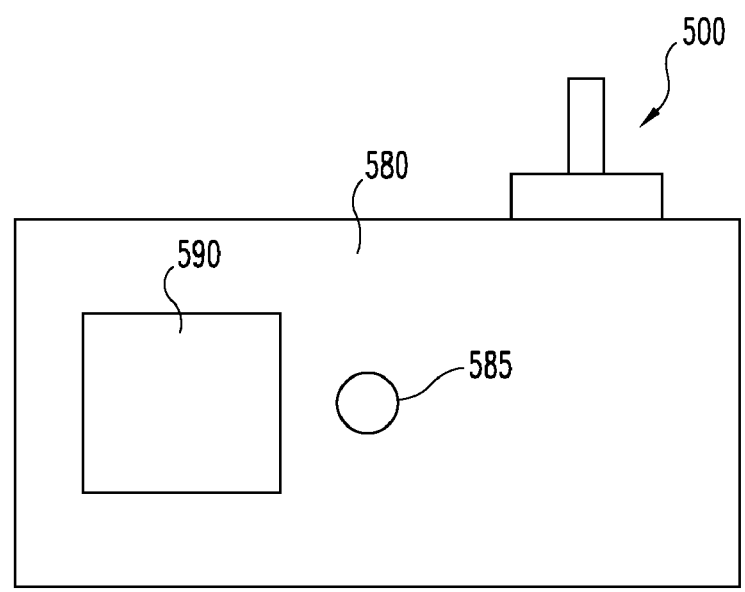
FIG. 5B is a side view of the apparatus shown in FIG. 5A disposed in a testing device.

In still another embodiment, shown in FIGS. 5A and 5B, apparatus 500 comprises a main body 505, lancet 520, lancet carrier 510, annular space 530 and biasing mechanism 550. In use (not shown), apparatus 500 is disposed over a site where body fluid is to be sampled, lancet 520 is advanced within main body 505 by applying a downward force D to lancet carrier 510. The distal end 535 of lancet 520 pierces the tissue, thereby creating a small incision through which body fluid will flow. Force D is then removed from lancet carrier 510, whereby biasing or resilient mechanism 550 retracts lancet 520 within main body 505. Body fluid flows from the incision created by the lancet into annular space 530 by capillary action.

After a sufficient amount of body fluid has been drawn into annular space 530, apparatus 500 is placed into analysis equipment, such as blood glucose measuring device 580 shown in FIG. 5B. The analysis equipment may use optical transmittance, reflectance, fluorescence or direct sampling with electrical and/or chemical stimuli to test the fluid sample in conventional fashion. For example, in a simple testing machine a blood glucose level is obtained by pressing button 585 on measuring device 580, resulting in a blood glucose level displayed on display 590.

In a still further embodiment also illustrated in FIGS. 5A and 5B, electro-chemical sensors or electrodes 560 may be located within annular space 130. The sensors 560 are connected by wires 565 to measuring equipment 580 to perform analysis of the body fluid. The sensors can be connected to the measuring equipment prior to the fluid acquisition, or unit 100 may be moved and placed in or connected to the measuring equipment.

Figure 6A:
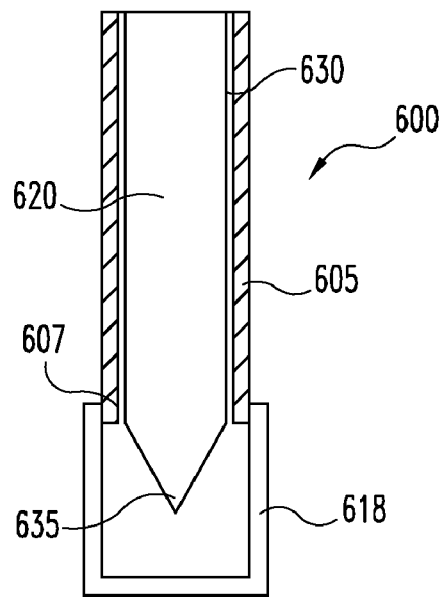
FIG. 6A is a cut-away side view of an alternate embodiment of the apparatus of the present invention.
Figure 6B:
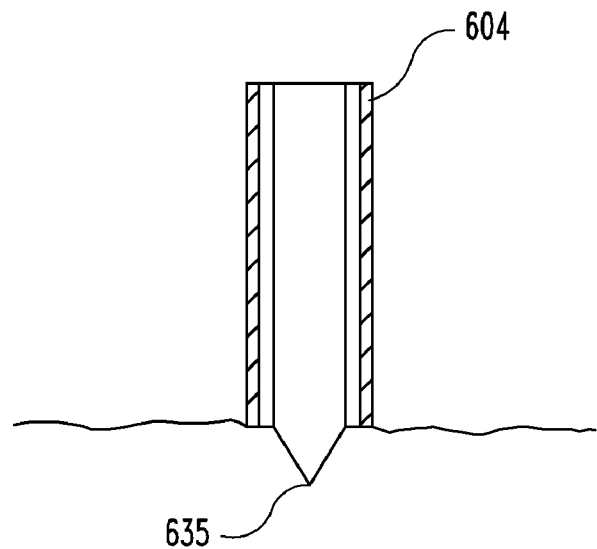
FIG. 6B is a cut-away side view of the apparatus of FIG. 6A disposed within a tissue surface.

A further variant on the structure of unit 100 is illustrated in FIGS. 6A and 6B. Apparatus 600 comprises main body 605, lancet 620, annular space 630 and safety cap 618 disposed over the end of main body 605. In this embodiment, the lancet 620 is secured to the main body, and does not move relative thereto. As shown in FIG. 6A, in apparatus 600 the distal end 635 of lancet 620 extends slightly beyond the distal end 607 of main body 605. Typically, the distance between the distal end 635 of lancet 620 and main body 605 is between 0.05 mm and 2 mm, preferably between 0.5 mm and 1.2 mm.

Figure 6C:
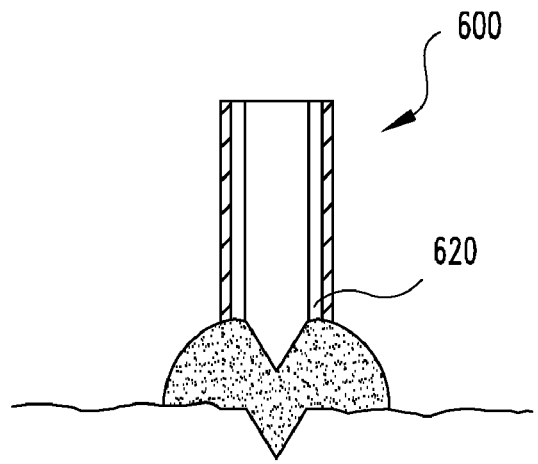
FIG. 6C is a cut-away side view illustrating the apparatus of FIG. 6A displaying the capillary action of the design.

In use as shown in FIG. 6B, after safety cap 618 is removed from the distal end 607 of main body 605, apparatus 600 is placed over a desired location where body fluid is to be withdrawn, i.e. forearm or fingertip. A force is applied to the proximal end 604 of main body 605, forcing the distal tip 635 of lancet 620 into the tissue and creating a small incision through which body fluid will flow. Apparatus 600 is then slightly retracted from the tissue location, as shown in FIG. 6C, allowing a small drop of body fluid to form and drawing the fluid into annular space 630 by capillary action. The fluid can then be tested in the various manners described herein.

A further alternate embodiment is illustrated in FIG. 7 with a disposable unit 700 held in a base 740. Unit 700 includes main body 705 with lancet 720 mounted to carrier 710. Main body 705 is preferably releasably held by interior wall 745 of base 740 by suitable means, such as a friction fit (shown) or other coupling. Carrier 710 extends to an injector member or plunger 760 and may be connected by a friction fit, threaded engagement, form fit, jigsaw fit (such as disclosed in PCT/EP01/12527), a snap or a similar coupling. Spring 750 is mounted between bearing surfaces 707 on base 740 and bearing surfaces 722 on injector 760. In this embodiment, the assembly provides a larger grippable area to facilitate use, while allowing a reusable base and minimizing the internal structure and pieces for a disposable unit 700. Various base unit designs, for example a "pen" injector, can also be used.

An additional preferred embodiment is illustrated in FIGS. 8A, 8B and 8C. Device 800 includes a proximal body portion 805 coupled to a distal body portion 807. Carrier 810 attached to lancet 820 is disposed within proximal body portion 805 with lancet 820 extending through distal body portion 807 to a distal tip. Capillary channel 830 is defined in distal body portion 807, and defines an annular space extending from the distal end of body portion 807 to a testing element holder 860. Preferably testing element holder 860 is a side port in body portion 807 for receiving testing media such as a testing pad 890.

Figure 9A:
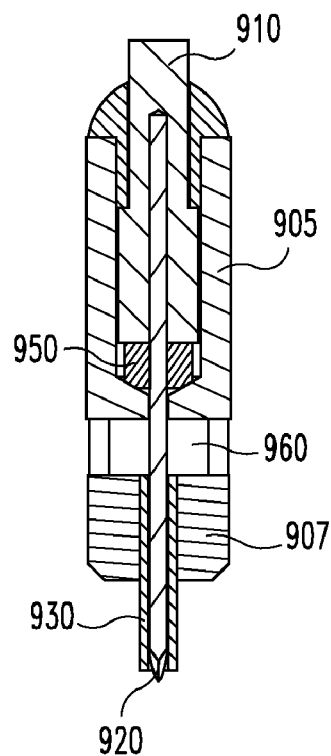
FIG. 9A is a cut-away side view of an alternate embodiment of the apparatus of the present invention.
Figure 9B:
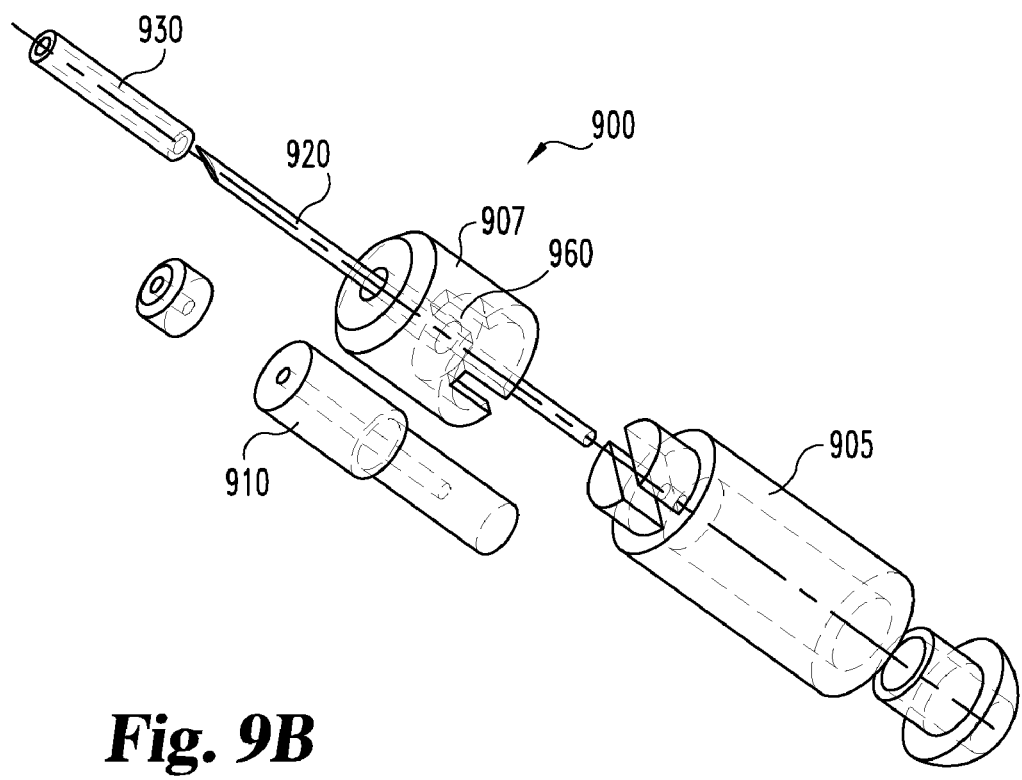
FIG. 9B is a disassembled view of the apparatus of FIG. 9A.

Another preferred embodiment is illustrated in FIGS. 9A and 9C. Device 900 includes a proximal body portion 905 coupled to a distal body portion 907. Carrier 910 attached to lancet 920 is disposed within proximal body portion 905. Capillary tube 930 surrounding lancet 920 and an annular space is received within distal body portion 907. Capillary 930 extends from the distal end of body portion 907 to a testing element holder 960. Preferably testing element holder 960 is a slot or side port in body portion 907.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A method, comprising:
    forming an incision in tissue by extending a lancet from a capillary member of an integrated unit, wherein the lancet is located inside the capillary member before said forming the incision;
    partially withdrawing the lancet from the incision in which a portion of the lancet remains within the incision;
    drawing body fluid from the incision into a capillary space defined between the capillary member and the lancet while the lancet is partially withdrawn within the incision, wherein the lancet acts as a focal point for drawing the body fluid into the capillary space; and
    depositing the body fluid onto a test strip that is disposed in the capillary space.

2. The method of claim 1, further comprising:
    fully withdrawing the lancet from the incision after said drawing the body fluid so that the entire lancet is located inside the capillary member.

3. The method of claim 1, further comprising:
    wherein said drawing the body fluid includes collecting less than 1 µl of the body fluid with the capillary member.

4. The method of claim 1, wherein the lancet is made in a solid piece that is sufficiently sharpened to form the incision.

5. The method of claim 1, wherein the capillary space between the lancet and the capillary member is between 20 to 200 µm to improve fill time.

6. The method of claim 1, further comprising:
    maintaining sterility of the lancet with a sealing member placed over an end of the capillary member; and
    removing the sealing member from the capillary member before said forming the incision.

7. The method of claim 1, further comprising:
    maintaining sterility of the lancet with a sealing member placed over an end of the capillary member; and
    piercing the sealing member with the lancet during said forming the incision.

8. The method of claim 7, wherein the sealing member includes a membrane.

9. The method of claim 1, wherein said forming the incision includes penetrating the tissue to a depth of 0.5 to 1.2 mm with the lancet.

10. The method of claim 1, wherein the test strip extends into the capillary space through a slot defined in the capillary member.

11. The method of claim 1, wherein the test strip is received in a groove in the lancet.

12. The method of claim 1, further comprising:
    analyzing the body fluid with the test strip.

13. The method of claim 1, wherein the capillary member includes a capillary tube.

14. The method of claim 1, further comprising:
    wherein the lancet is made in a solid piece that is sufficiently sharpened to form the incision;
    wherein the capillary member includes a capillary tube;
    maintaining sterility of the lancet with a sealing member placed over an end of the capillary member; and
    piercing the sealing member with the lancet during said forming the incision;
    wherein said forming the incision includes penetrating the tissue to a depth of 0.5 to 1.2 mm with the lancet;
    fully withdrawing the lancet from the incision after said drawing the body fluid so that the entire lancet is located inside the capillary member;

wherein said drawing the body fluid includes collecting less than 1 μl of the body fluid with the capillary member; and wherein the capillary space between the lancet and the capillary member is between 20 to 200 μm.

15. A method, comprising:

forming an incision in tissue with an integrated unit that includes a lancet received in a capillary member by moving the lancet longitudinally between a retracted position where the lancet is retracted inside the capillary member and an extended position where the lancet extends from the capillary member;

moving the lancet from the extended position to a partially withdrawn position where a portion of the lancet remains within the incision;

drawing body fluid from the incision into a capillary space defined between the capillary member and the lancet while the lancet is at the partially withdrawn position;

depositing the body fluid onto a test strip that is disposed in the capillary space; and retracting the lancet to the retracted position after said drawing the body fluid.

16. The method of claim 15, further comprising:

wherein said drawing the body fluid includes collecting less than 1 μl of the body fluid with the capillary member.

17. The method of claim 15, wherein the capillary space between the lancet and the capillary member is between 20 to 200 μm to improve fill time.

18. The method of claim 15, further comprising:
analyzing the body fluid with the test strip.

19. The method of claim 15, wherein the test strip is received in a groove in the lancet.

20. The method of claim 15, further comprising:

wherein the lancet is made in a solid piece that is sufficiently sharpened to form the incision;

wherein the capillary member includes a capillary tube;

maintaining sterility of the lancet with a sealing member placed over an end of the capillary member; and piercing the sealing member with the lancet during said forming the incision;

wherein said forming the incision includes penetrating the tissue to a depth of 0.5 to 1.2 mm with the lancet;

wherein said drawing the body fluid includes collecting less than 1 μl of the body fluid with the capillary member; and wherein the capillary space between the lancet and the capillary member is between 20 to 200 μm.

* * * * *